United States Patent [19]

Yin

[11] 4,404,469

[45] Sep. 13, 1983

[54] REAL-TIME 3-D X-RAY AND GAMMA-RAY VIEWER

[75] Inventor: Lo I. Yin, Silver Spring, Md.

[73] Assignee: The United States of America as represented by the United States National Aeronautics and Space Administration, Washington, D.C.

[21] Appl. No.: 267,178

[22] Filed: May 22, 1981

[51] Int. Cl.³ .............................................. G01T 1/20
[52] U.S. Cl. ............................ 250/363 R; 250/363 S; 250/368; 378/2
[58] Field of Search ................. 250/363 R, 363 S, 367, 250/368, 369; 378/2

[56] References Cited

U.S. PATENT DOCUMENTS 4,142,101  2/1979  Yin ....................................... 250/363
4,360,797  11/1982  Fenimore et al. ................. 250/363 S

OTHER PUBLICATIONS

Chang et al., "A Method of Tomographic Imaging Using a Multiple Pinhole-Coded Aperture", *J. Nucl. Med.* vol. 15, No. 11 (Nov. 1974) p. 1063.
Three-dimensional imaging of x-ray and gamma-ray objects in real time, Yin et al., Applied Optics, vol. 19, No. 17, Sep. 1, 1980.
Wide-angle Integral Photography-The Integram System, R. L. de Montebello, SPIE vol. 120 Three Dimensional Imaging (1977).

*Primary Examiner*—Janice A. Howell
*Attorney, Agent, or Firm*—John O. Tresansky; John R. Manning; Robert E. Bushnell

[57] ABSTRACT

A multi-pinhole aperture lead screen (22) forms an equal plurality of invisible mini-images having dissimilar perspectives of an x-ray and gamma-ray emitting object (ABC) onto a rear-earth phosphor layer (24) which, in turn, provides visible light mini-images directly into a visbile light image intensifier (26). A viewing screen (34/48) having an equal plurality of dissimilar perspective apertures distributed across its face in a geometric pattern identical to the lead screen, provides a viewer with a real, pseudoscopic image (A'B'C') of the object with full horizontal and vertical parallax. Alternatively, a third screen (34) identical to the viewing screen (48) and spaced apart from a second visible light image intensifier (42), may be positioned between the first image intensifier (26) and the viewing screen (48), thereby providing the viewer with a virtual, orthoscopic image (A"B"C") of the object (ABC) with full horizontal and vertical parallax.

19 Claims, 4 Drawing Figures

REAL-TIME 3-D X-RAY AND GAMMA-RAY VIEWER

ORIGIN OF THE INVENTION

The inventor described herein was made by an employee of the United States Government and may be manufactured and used by or for the Government for governmental purposes without the payment of any royalties thereon or therefor.

TECHNICAL FIELD

This invention pertains to invisible radiant energy imaging and, more particularly, to conversion of x-rays and gamma-rays emitted by an object into visible autostereoscopic, images of the object in real-time.

BACKGROUND ART

The contributions of modern physics have increased the availability of radioactive x-ray and gamma-ray emitting materials in industry and nuclear medicine. As radioactive emission principally occurs outside of the visible part of the electromagnetic spectrum, an unaided human observer is unable to "see" a source of radioactive emission. It is difficult, therefore, to distinguish a source of x-ray and gamma ray emission from non-emitting neighboring and visually similar objects. Various techniques exist to locate a source of radioactive emission. One technique requires trial and error search with a Geiger counter. Another technique uses a scintillation detector. The information provided by these techniques is limited to the intensity and location of radioactive emission, and reveals nothing about the shape of a radioactive object or the distribution of radioactivity within the object. An x-ray camera formed by placing x-ray sensitive film behind a pinhole in an x-ray shield merely provides a recording of a two-dimensional facsimile of an x-ray or gamma-ray emitting object in one perspective. The facsimile can be viewed only after a delay for processing of the film. Furthermore, a single pinhole aperture camera is rendered extremely inefficient by the minute aperture of the pinhole.

Other, existing x-ray or gamma-ray cameras employ either parallel or converging collimators to bring an essentially parallel beam projection of a radioactive object onto a detector. The detector may be in the nature of a film, a scintillator, or a phosphor material which converts x-rays and gamma-rays into visible light. The visible light generated, together with positional information, is then processed by any of a wide variety of methods using such devices as photomultiplier tubes (e.g., Anger cameras), image intensifiers, visible light cameras, video cameras, and centroid-computing electronics in various combinations. Without the additional steps of making successive exposures and subsequent reconstructions, a particular object-to-camera geometry provides only a two-dimensional single perspective image of an x-ray or gamma-ray emitting object. Although a steroscopic pair of such cameras may be used to obtain a stereoscopic pair of images which, upon reconstruction, provide a stereoscopic view of a single perspective of an object, that view lacks full horizontal and vertical parallax.

An earlier invention, a low intensity x-ray image scope ("Lixiscope") disclosed in U.S. Pat. No. 4,142,101, is a fully portable, hand-held device which provides an intensified visible-light image of objects illuminated with point sources of x-rays or gamma rays. It uses an x-ray to visible-light converter to drive a visible-light image intensifier having one or more microchannel plate electron multipliers. The Lixiscope provides a viewer with a visible shadow, in real time, of the illuminated objects.

STATEMENT OF THE INVENTION

Accordingly, it is an object of this invention to provide a device giving visible, three dimensional images with both horizontal and vertical parallax of x-ray and gamma-ray emitting objects.

It is another object to provide a device giving visible, three dimensional images with both horizontal and vertical parallax in real-time of x-ray and gamma-ray emitting objects.

It is yet another object to provide a device giving visible, three dimensional images in a single step with both horizontal and vertical parallax of x-ray and gamma-ray emitting objects.

It is still another object to provide a device giving visible, three dimensional, real pseudo-scopic images with horizontal and vertical parallax in real-time of x-ray and gamma-ray emitting objects.

It is a further object to provide a device giving visible, autostereoscopic, virtual orthoscopic images in real time of x-ray and gamma-ray emitting objects.

It is a still further object to provide a device giving visible, autostereoscopic images of true size of x-ray and gamma-ray emitting objects.

It is a yet further object to provide a device giving directly viewable, autostereoscopic images of true size of x-ray and gamma-ray emitting objects.

Briefly, these and other objects are achieved with a device having a pair of multiple-pinhole aperture plates held spaced apart from the opposite ends of an x-ray to visible-light converter mated to a visible-light image intensifier. When the output of the image intensifier is viewed through the second aperture plate, this device provides real three dimensional, pseudoscopic (i.e., reversed depth) images of x-ray and gamma ray emitting objects in real time. The images possess both horizontal and vertical parallax with a reasonably large field of view. Alternatively, the device may be modified to incorporate a second visible-light image intensifier equidistantly spaced between the second aperture plate and a third multiple-pinhole aperture plate aligned with the pinholes of the first aperture plate. When the output of the second image intensifier is viewed through the third aperture plate, the modified device provides virtual, three dimensional, orthoscopic (i.e., true depth) images also possessing horizontal and vertical parallax over a large field of view, during real time.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE DRAWINGS

Figure 1:
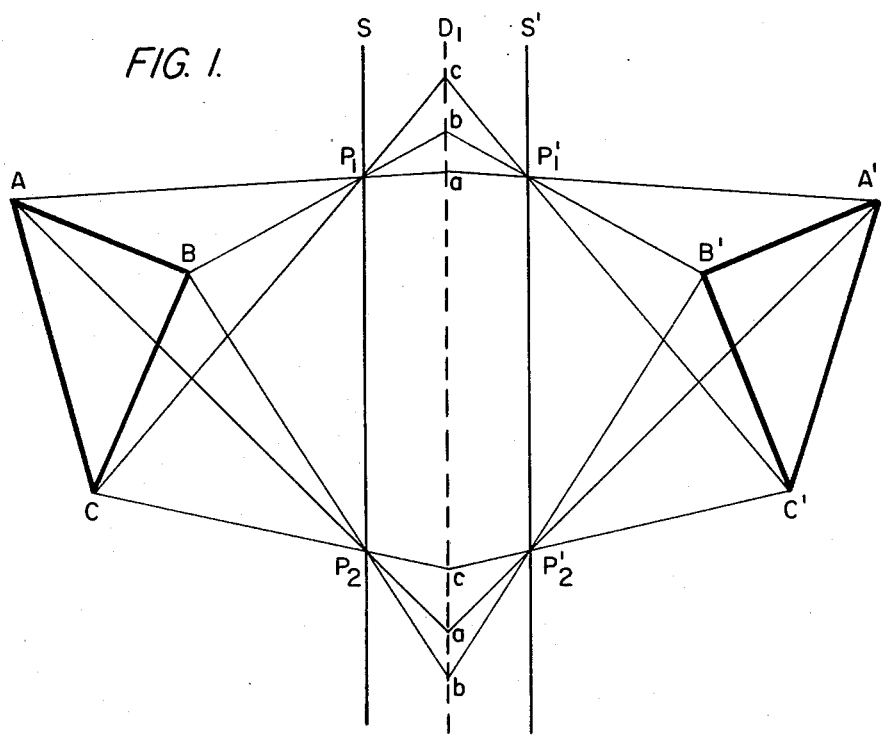
FIG. 1 is a schematic representation of the principle of three dimensional imaging of an object.

Refer now to the drawings and, in particular, to FIG. 1 where a pinhole screen analogy illustrates the principle of three dimensional imaging used in the present invention. A x-ray or gamma-ray emitting object ABC is situated in front of a screen S containing a multiplicity of pinhole apertures spaced apart in a planar array. Screen S is made of a material otherwise impervious to x-rays and gamma-rays. A non-inverting x-ray imaging detector $D_1$ is placed in position with its input surface at the input plane of screen S, parallel to and a short distance from the right of screen S, to convert x-ray and gamma-ray images into intensified visible light images at unity magnification. Each pinhole individually operates as a pinhole camera. By using pinholes $P_1$ and $P_2$ as an exemplary pair, two inverted x-ray mini-images abc of object ABC form on the receiving or input surface of detector $D_1$. These mini-images are converted into intensified visible-light images abc at the emitting or output surface of detector $D_1$. The separations between adjacent pinholes $P_1$ and $P_2$ and between S and $D_1$ are chosen so that the mini-images abc do not significantly overlap each other. A second screen, S', is positioned at the same distance from the output surface of detector $D_1$ as screen S is from the input surface of detector $D_1$. Screen S' contains a plurality of pinhole apertures distributed across its surface in a planar array preferably identical to and aligned with the array of pinholes in screen S. Screen S' is made from a material opaque to visible light.

When viewed through pinholes $P_1'$ and $P_2'$, spatially corresponding to and aligned with pinholes $P_1$ and $P_2$, the mini-images abc will form a visible light recontruction A'B'C' of the x-ray or gamma-ray emitting object ABC. The reconstructed image A'B'C' is a real image situated in front of screen S' toward the viewer, with a magnification of unity. Although the image A'B'C' is an upright image, it is pseudoscopic, that is, the depth of the object ABC is reversed when viewed through screen S'. For instance, in FIG. 1 it can be seen that point B' is now away from the viewer rather than toward the viewer as point B is in object ABC. Screen S contains many pinholes like $P_1$ and $P_2$, each having a slightly different perspective view of the object ABC. Therefore, the reconstructed image A'B'C' may be viewed through screen S' over a range of different directions, thereby providing a viewer with both horizontal and vertical parallax. The reconstructed image A'B'C' is, therefore, truly three-dimensional or autostereoscopic. This three-dimensional effect is most pronounced when the object viewed fills the field-of-view defined by the distance between the pinholes and the separation between screen S and detector $D_1$. In the configuration shown in FIG. 1, the field-of-view is that field providing the largest mini-images abc possible without overlap occurring between adjacent mini-images.

Figure 2:
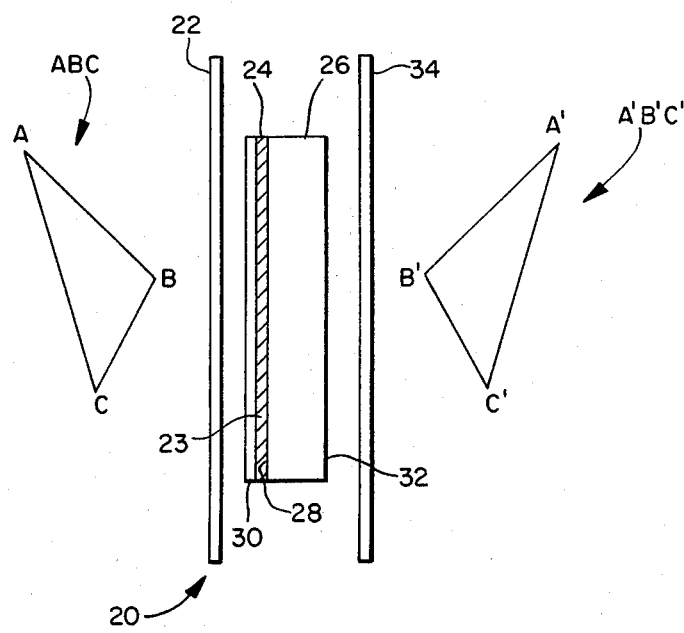
FIG. 2 is a block diagram showing the functional elements of one embodiment of the invention.

FIG. 2 shows the major functional elements of an optical instrument 20 providing a real, three dimensional image of an x- or gamma-ray emitting object ABC in real time based on the principle illustrated in FIG. 1. A screen 22, made from a thin sheet of a material, such as lead, impervious to x-rays and gamma rays and perforated by numerous pinholes of equal area (too small to be shown) uniformily distributed over the surface of the screen, is placed between object ABC and a thin rare-earth phosphor or scintillator layer 24. Each pinhole serves as a separate pinhole camera and produces an inverted mini-x-ray image of the object ABC on converter layer 24. The pinholes are spaced so that the mini-images do not significantly overlap each other. Converter layer 24 is a scintillator or rare-earth phosphor, which serves to convert x-ray and gamma-ray images incident upon it into visible-light images. The visible-light images generated by converter layer 24 are applied directly onto a non-inverting visible-light image intensifier with its input surface 28 positioned immediately next to converter layer 24. A thin shield 30, made from a material opaque to visible light but transparent to x-rays and gamma-rays (e.g., black plastic film), is positioned, between screen 22 and converter layer 24 and fitted to cover the entire input surface 23 of converter layer 24, to block visible light from reaching the input surface 28.

A second or viewing screen 34, also perforated by numerous pinhole apertures (too small to be shown) distributed in an array preferably identical to and aligned with that of screen 22, is spaced apart from the output surface 32 of image intensifier 26 by approximately the same distance as screen 22 is separated from converter layer 24. Screen 34 is made from a material opaque to visible light, such as aluminum. Unlike screen 22, screen 34 is not necessarily impervious to x-rays and gamma-rays. When the intensified visible-light mini-images at the output surface 32 of image intensifier 26 are viewed through screen 34, a real erect pseudoscopic image A'B'C' is reconstructed. This reconstructed visible light image A'B'C' is situated suspended in space, toward the viewer, with about the same separation from screen 34 as object ABC is from screen 22. The depth of image A'B'C' may be magnified without disturbing its lateral dimensions by moving viewing screen 34 farther from emitting surface 32 of intensifier 26. Screen 22 may be fixed in its separation from converter 24 by a glass or plastic spacer (not shown) which also serves as support for screen 22.

Together, x-ray and gamma-ray to visible light converter 24 and visible-light image intensifier 26 perform the function of detector $D_1$ of FIG. 1 while screens 22 and 34 serve as screens S and S', respectively. With an image intensifier 26 producing a non-inverted image of unity magnification, both the orientation and size of the incident mini-images abc arriving at the detector input surface 28 of image intensifier 26 are preserved at the output surface 32; however, at the emitting surface 32, they are in the form of intensified visible light mini-images. Mini-images abc in FIG. 1 therefore represent both the input and output of x-ray imaging detector $D_1$.

Figure 3:
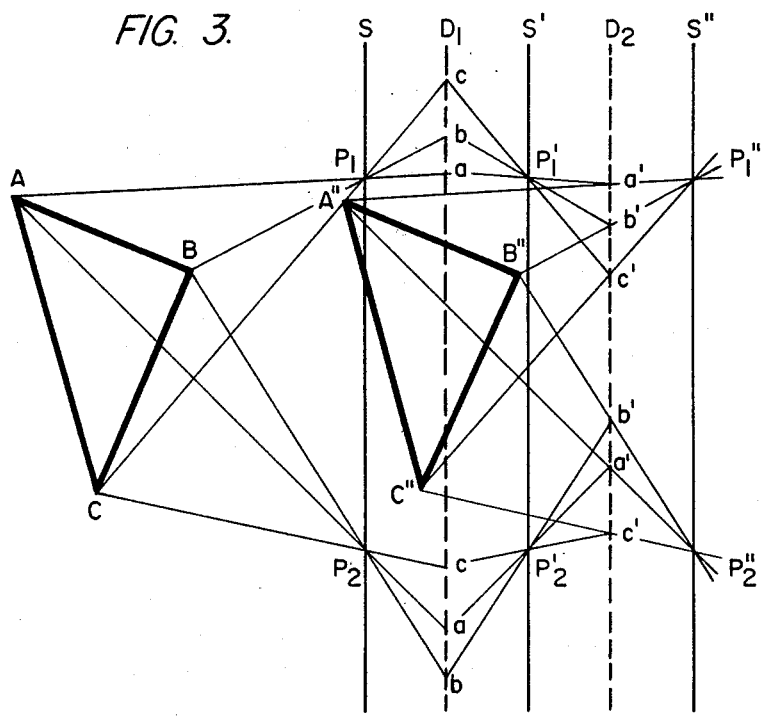
FIG. 3 is a schematic representation of the principle of producing an orthoscopic three dimensional image of an object.
Figure 3:

Turning now to FIG. 3, a schematic of another pinhole screen analogy shows that an orthoscopic image of an x-ray or gamma-ray emitting object ABC may be obtained utilizing the principle illustrated in FIG. 1 by the additional step of performing a point-by-point inversion of mini-images abc. It is to be noted that a collective inversion of the mini-images abc will not provide an orthoscopic image. It is therefore, necessary to make a point-by-point inversion of mini-images abc from the output of detector $D_1$ to obtain the desired orthoscopic image A"B"C" from mini-images a'b'c'. This step may be performed by placing a second non-inverting, visible light image intensifier $D_2$ approximately the same distance from the screen $S'$ as the detector $D_1$ is from screen $S'$. Now, screen $S'$ acts as an inverting screen rather than a viewing screen and the mini-images abc from detector $D_1$ are inverted through pinholes $P_1'$ and $P_2'$ into images a'b'c' at the surface of intensifier $D_2$. A third screen $S''$, preferably identical to screen $S'$, is placed at approximately the same distance from the intensifier $D_2$ as screen $S'$ is to intensifier $D_2$. Screen $S''$ has pinholes $P_1''$ and $P_2''$ therein aligned with pinholes $P_1'$ and $P_2'$ in screen $S'$. It is to be noted that this pinhole screen analogy relies upon pinhole aperture screen $S'$ to invert mini-images abc rather than to use those mini-images to reconstruct pseudoscopic image A'B'C'.

When mini-images a'b'c' are viewed from the right of screen $S''$ through pinholes $P_1''$ and $P_2''$, the rays of mini-images a'b'c' are now divergent in the direction of the viewer. Consequently, a virtual, orthoscopic image A''B''C'' of object ABC is formed to the left of screen $S''$. This orthoscopic (true depth) virtual image is situated to the left of the viewing screen $S''$ at approximately the same distance as object ABC is from screen S. Thus, when looking at screen $S''$, the viewer receives a sensation of seeing object ABC through a "window."

Figure 4:
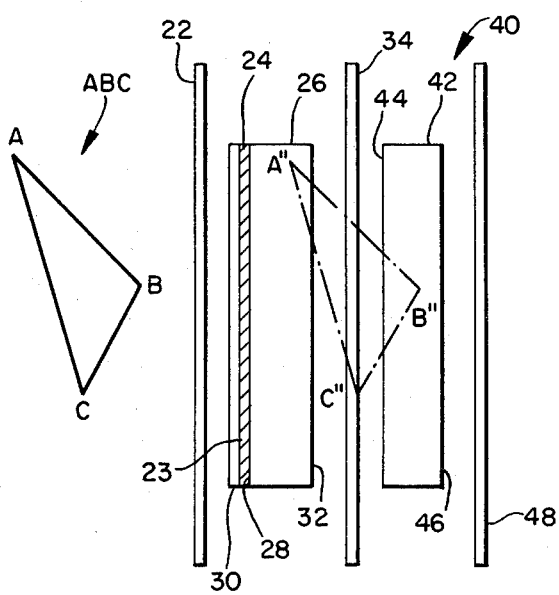
FIG. 4 is a block diagram showing the functional elements of an alternative embodiment of the invention.
Figure 4:

Referring now to FIG. 4, optical instrument 40 thereof is a two stage alternative embodiment designed to translate pseudoscopic image A'B'C' into an orthoscopic image A''B''C'' according to the principle illustrated in FIG. 3. Instrument 40 differs from instrument 20 by the incorporation of a second stage having a second non-inverting, visible light intensifier 42 with its input surface 44 spaced apart from a second screen 34 by a distance approximately equal to the distance between screen 34 and output surface 32. Unlike intensifier 26, the input surface 44 of intensifier 42 is not mated with a x-ray to visible light converter. Image intensifier 42 receives the inverted mini-images a'b'c' produced by the pinhole apertures in screen 34 and displays those images, much intensified, with unity magnification on its output surface 46. A third or viewing screen 48, also perforated by numerous pinhole apertures forming a planar array preferably identical to that of screen 34, is spaced apart from the output surface 46 by a distance approximately equal to the distance between screen 34 and input surface 44. A virtual, orthoscopic image A''B''C'' may then be viewed through screen 48. The depth of image A''B''C'' may be magnified without disturbing its lateral dimensions by moving screen 48 farther from the emitting surface 46 of light intensifier 42.

Alternatively, if pinhole aperture screens 34 and 48 are made identical, instrument 20 may be constructed so that viewing screen 34 slides to the right, permitting insertion of pinhole screen 48 and image intensifier 42 between intensifier 26 and screen 34.

FIGS. 1 and 3 illustrate the principles underlying operation of the present invention. Specific implementation of these principles may vary. For example, variation in the implementation may occur in such component parts as the pinhole aperture screens or in the visible light image intensifiers. Preferably, the apertures through screens 22, 34 and 48 are arranged in planar arrays of similar and preferably identical, patterns. The patterns may be either uniform or irregular. Typically, the number of apertures in and the surface areas of each screen will be equal if the instrument 20, 40 is designed to provide unity magnification. In an instrument providing other than unity magnification (e.g., minification) however, if the patterns are similar or identical, the surface area and, therefore, the spacing between apertures of at least one screen may differ from the other screens. The screens 22, 34 and 48 should be assembled in instruments 20, 40 to assure near alignment between apertures in neighboring screens. To provide an acceptable quality of image, overlapping of mini-images abc, a'b'c' at the input-planes 23, 44, respectively, should be avoided by maintaining minimum separation between the screens and detectors and by using a geometric aperture pattern which provides sufficient separation between adjacent pinholes in each array. Additionally, the cross-sectional areas of the pinholes must be uniform and large enough, 0.2–0.3 mm for a 0.5 mm thick screen, to avoid diffraction effects in the visible-light range. Similarly, the diameter of all pinholes should be equal because the intensity of an image seen through a pinhole is dependent upon the cross-sectional diameter of the pinhole.

A modification of instruments 20, 40 in which a large aperture optical lens, e.g. a double convex lens, is inserted between converter layer 24 and the input surface 28 of visible-light image intensifier 26, enables the instrument to provide magnification other than unity. In this modification, shield 30 is correspondingly extended to prevent stray visible light from entering between converter layer 24 and image intensifier input surface 28. The optical lens focuses mini-images from converter layer 24 onto input surface 28, thereby allowing converter layer 24 and input screen 22 to have surfaces differing in area from the input surface area 28 of image intensifier 26. Thus, larger objects ABC may be viewed with the instrument. Similar modifications may be made at the viewing end of instruments 20, 40.

Any of several commercially available devices may be used in instruments 20, 40 as visible light image intensifiers 26, 42. One class of such devices is the proximity focused typed. Another class is the inverter type which has either electrostatic or magnetic lenses with varying magnification factors. A third class of visible light intensifiers is exemplified by the microchannel plate visible-light intensifier disclosed in U.S. Pat. No. 4,142,101. Some of these commercially available image intensifiers may include an internal x-ray to visible light converter 24 while others are made with a converter 24 mounted just outside an exterior envelope at the input surface.

It is to be noted that the noun "pinhole" is used here to indicate an essentially non-diffracting non-focused, x-ray, gamma-ray or visible-light aperture. The adjectives "visible" and "invisible" refer, respectively, to whether or not the spectrum of the radiant electromagnetic energy discussed is normally discernible with unaided human vision. The nouns "light" and "light beam" are used to indicate radiant electromagnetic energy within the visible spectrum while the noun "ray" indicates radiant electromagnetic energy within the x-ray and gamma-ray region of the invisible spectrum.

An optical instrument has been disclosed having an x-ray to visible-light converter mated to a visible-light intensifier with a pair of screens equidistantly spaced apart ($\sim$1.6 mm) from either end of the converter-intensifier. In this configuration, the planar array of pinholes ($\sim$1000, 0.3 mm each in diameter) uniformly distributed (in hexagonal pattern, for instance, with 1.6 mm center-to-center spacing) over the face of the first screen partitions the view of an invisible ray emitting object into a plurality of dissimilar mini-images discretely distributed over the face of the converter. Through the second screen, ideally identical to the first, a visible-light image of the object is reconstructed from an equal plurality of dissimilar mini-images, thereby providing an erect, three-dimensional pseudoscopic image with both horizontal and vertical parallax directly viewable over a wide field of view during real time by one or more human observers. An orthoscopic visible-light image may also be obtained for real-time viewing by the simple addition of one more stage of a visible light image intensifier and a viewing screen.

The three-dimensional sensation of depth provided by instruments 20, 40 may be enhanced by increasing the distance between viewing screen 34 or 48, respectively, and the output surfaces 32 or 46. Increasing this separation causes magnification of the depth of the reconstructed image without disturbing its lateral dimensions. Concurrently with increasing separation between the viewing screen and image intensifier output surface however, a decrease in angular separation between zero and higher order images occurs because the decrease in angular separation permits images on the output surface to become visible through one or more of the neighboring pinhole apertures of the viewing screen.

It will be appreciated that all those changes and modifications which fall fairly within the scope of the invention shall be a part thereof. For example, although the embodiments of the invention are disclosed as providing unity magnification, the use of minifying light intensifiers may be substituted for intensifiers 26, 42, thereby providing magnification other than unity. Similarly, either longer decay time phosphor layers, storage oscilloscopes, or digitizing instruments may be used in place of the emitting phosphor layer 32, 46 in light intensifiers 26, 42 to provide longer integration times. Further, a finer grain phosphor will provide increased image resolution. Additionally, although pinhole apertures are necessary in initial screen 22, viewing screen 34 and orthoscopic screen 48 may either be modified to incorporate or replaced by bubble lenses, lenticulated sheets or multiple optical lenses to increase output transmission while improving viewing quality.

The pinhole apertures of screens 22, 34, 48 are preferably made uniform to assure the quality of reconstructed images A'B'C', A"B"C". A plurality of discrete apertures rather than collimator channels, are used in screens 22, 34, 48 because each aperture provides a view of the complete object while each collimator channel would provide a view of but a portion of the object. As each aperture in an array has a different perspective view, an array of apertures inherently provides a three dimensional image of an object. The apertures of inverting screen 34 and viewing screen 48 need not be pinholes however, as several types of optical lenses may also be used. Either a lenticulated sheet, an array of discrete thin or thick lenses, or a sheet of discrete bubble lenses may be substituted for pinhole aperture screen arrays 34, 48.

Further details about the use and construction of instruments 20 and 40 may be found in a paper entitled "Three-dimensional imaging of x-ray and gamma-ray objects in real time," by L. I. Yin, J. I. Trombka and S. M. Seltzer, published in Applied Optics, volume 19, number 17, during 1980. X-ray screen 22 and viewing screen 34, 48 in instruments 20, 40 may be curved with equal but oppositely sensed radii of concave curvature facing the object ABC and pseudoscopic image A'B'C', respectively. As applied to two stage instrument 40, however, curved screens 22, 48 necessitate an increasing center-to-center spacing between adjacent pinhole (or lens) apertures in inverting screen 34 as a function of distance from the center of screen 34. Converter 24, image intensifiers 26, 48 and inverting screen 34 retain their planar surfaces if screens 22, 48 are curved, although their surface areas may be increased to take advantage of the higher resolution of the peripheral mini-images provided by curved x-ray screen 22.

It is apparent that the disclosed instruments provide an immediate, three-dimensional image of x-ray and gamma-ray emitting objects that are likely to be otherwise undiscernible to human observers. The small size of these instruments allows them to be made fully portable, suitable for such use as providing a welding inspector with a real-time image of the precise shape of a smaller radioactive section of a larger object, such as a length of contaminated pipe in a nuclear power plant. Or, to provide a physician with an in situ, three-dimensional image of a radioactive isotope absorbing cancerous section of a human gland. Additionally, the field-of-view provided by these instruments allows more than one person to simultaneously view the three-dimensional images generated. 9n

What is claimed is:

1. An instrument for viewing x-ray and gamma-ray emitting objects, comprising:
   means (22) for forming incident x-rays and gamma-rays emitted by an object into an array of mini-images of said object;
   means (24) spatially displaced from said forming means (22) for converting said x-ray and gamma-ray mini-images into visible-light mini-images;
   first means (26) coupled to said converting means (24) for intensifying said visible-light mini-images; and
   screening means (34/48) having a plurality of apertures, spatially displaced from said first intensifier means (26), for providing a reconstructed autostereoscopic visible-light image of said object having a continuum of perspective views.

2. An instrument for viewing x-ray and gamma-ray emitting objects, comprising:
   means (22) for forming from x-rays and gamma-rays emitted by an object a plurality of mini-images having dissimilar perspective views of said object;
   means (24) spatially displaced from said forming means (22) for converting said x-ray and gamma-ray mini-images into visible-light mini-images;
   first means (26) conjugately paired with said converting means (24) for intensifying said visible-light mini-images; and
   screening means (34) having a plurality of apertures, spatially displaced from said first intensifying means (26), for reconstructing from said intensified visible-light mini-images a composite pseudoscopic image of said object, having both vertical and horizontal parallax.

3. The instrument of claims 1 or 2 wherein said forming means (22) includes a plurality of apertures having dissimilar perspective of said object.

4. The instrument of claim 3 wherein said forming means (22) and said screening means (34) have equal pluralities of said apertures.

5. The instrument of claim 3 wherein said forming means (22) and said screening means (34) have equal pluralities of said apertures distributed in arrays of identical geometric pattern.

6. An instrument for viewing x-ray and gamma-ray emitting objects, comprising:
means (22) for forming incident x-rays and gamma-rays emitted by an object into an array of mini-images of said object;
means (24) spatially displaced from said forming means (22) for converting said x-ray and gamma-ray mini-images into visible-light mini-images;
first means (26) proximate to said converting means (24) for intensifying said visible-light mini-images;
screening means (34) having a plurality of apertures, spatially displaced from said first intensifier (26), for inverting each of said plurality of intensified visible-light mini-images provided by said first intensifying means (26);
second means (42) spatially displaced from screening means (34), for intensifying said plurality of inverted visible-light mini-images; and
viewing means (48) having a plurality of apertures, spatially displaced from said second intensifier means (42), for reconstructing from said intensified plurality of inverted visible-light mini-images a composite orthoscopic image of said object, having vertical and horizontal parallax.

7. The instrument of claim 6 wherein said viewing means (48) and said screening means (34) have equal pluralities of said apertures.

8. The instrument of claim 6 wherein said viewing means (48) and said screening means (34) have equal pluralities of said apertures distributed in planar arrays of identical geometric pattern.

9. The instrument of claim 6 wherein said viewing means (48), said screening means (34) and said forming means (22) have equal pluralities of said apertures.

10. The instrument of claim 6 wherein said viewing means (48), said screening means (34) and said forming means (22) have equal pluralities of said apertures distributed in aligned arrays.

11. The instrument of claim 6 wherein said viewing means (48) is spatially disposed between said first intensifying means (26) and said screening means (34), for inverting each of said plurality of intensified mini-images provided by said first intensifying means via said plurality of uniform apertures; and
said second intensifying means (42) is spatially disposed between said viewing means (48) and said screening means (34);
whereby said screening means (34) reconstructs from said intensified plurality of inverted visible-light mini-images a composite orthoscopic image of said object, having vertical and horizontal parallax.

12. The instrument of claim 11 wherein said viewing means (48) and said screening means (34) have equal pluralities of said apertures.

13. The instrument of claim 11 wherein said viewing means (48) and said screening means (34) have equal pluralities of said apertures distributed in planar arrays of identical geometric pattern.

14. The instrument of claim 11 wherein said viewing means (48), said screening means (34) and said forming means (22) have equal pluralities of said apertures.

15. The instrument of claim 11 wherein said viewing means (48), said screening means (34) and said forming means (22) have equal pluralities of said apertures distributed in aligned arrays.

16. An instrument for viewing x-ray and gamma-ray emitting objects, comprising:
a first plate of a material impenetrable to x-rays and gamma-rays, having a planar array of discrete apertures of equal cross-sectional area for passage of x-rays and gamma-rays emitted by an object;
means spaced apart in a plane parallel to said first plate, for converting said x-rays and said gamma rays passed by said first plate into visible light;
a first image intensifier coupled to said converting means to receive said visible light and emit intensified visible-light mini-images; and
a second plate spaced apart in a plane parallel to said first image intensifier opposite said converting means and having an array of discrete apertures of equal cross-sectional area for viewing a three-dimensional image of said object reconstructed from said intensified visible-light mini-images.

17. The instrument of claim 16, further comprising:
a third plate disposed between said first image intensifier and said second plate, having an array of discrete apertures of equal cross-sectional area providing individual inversion of intensified visible-light mini-images emitted by said first image intensifier; and
a second image intensifier disposed between said second and said third plates to receive and provide intensification of said intensified visible-light mini-images inverted by said third plate.

18. The instrument of claim 16 wherein said arrays of apertures in said first and said second plates are distributed across surfaces of said first and said second plates in an identical pattern.

19. The instrument of claim 16 wherein said first image intensifier has an emitting surface adjacent and spaced apart from said second plate and said first and said second plates are spaced apart from said converting means and said emitting surface by equal distances.

* * * * *